United States Patent [19]

Stalcup

[11] Patent Number: 5,052,925
[45] Date of Patent: Oct. 1, 1991

[54] DENTAL MIRROR AND METHOD OF USING SAME

[76] Inventor: Robert W. Stalcup, 21152 Peppertree La., Mission Viejo, Calif. 92691

[21] Appl. No.: 462,786

[22] Filed: Jan. 10, 1990

[51] Int. Cl.⁵ .............................................. A61B 1/24
[52] U.S. Cl. ....................................................... 433/30
[58] Field of Search ........................... 433/30, 31, 140; 128/21, 22; 350/640, 600

[56] References Cited

U.S. PATENT DOCUMENTS

| | | | |
|---|---|---|---|
| 548,817 | 10/1895 | Platt | 433/31 |
| 1,021,639 | 3/1912 | Smith | 433/30 |
| 3,300,859 | 1/1967 | Sanden | 433/33 |
| 4,090,506 | 5/1978 | Pilgrim | 433/31 |
| 4,500,169 | 2/1985 | Donnelly | 350/600 |

FOREIGN PATENT DOCUMENTS

| | | | |
|---|---|---|---|
| 69302 | 6/1940 | Czechoslovakia | 350/640 |
| 193683 | 5/1967 | U.S.S.R. | 128/21 |

*Primary Examiner*—John J. Wilson
*Attorney, Agent, or Firm*—Knobbe, Martens, Olson & Bear

[57] ABSTRACT

An improved dental mouth mirror has an oval mirrored surface to increase the number of teeth which can be viewed and improve illumination of the mouth and the retraction of oral tissues, but avoids the concomitant obstruction inherent in larger, conventional round dental mouth mirrors. The major axis of the oval mirrored surface is inclined by approximately 75° from the longitudinal axis of the mirror handle to allow adjustment of the field of vision by merely rotating the hand of the operator to change the angle of the mirror handle, thereby obviating the need for axial movement of the mirror handle. The mirrored surface is provided with spaced parallel reference lines for aligning a first reference line with a first tooth surface and comparing a second reference line with a second tooth surface so as to determine parallelism of said first and second tooth surfaces.

10 Claims, 2 Drawing Sheets

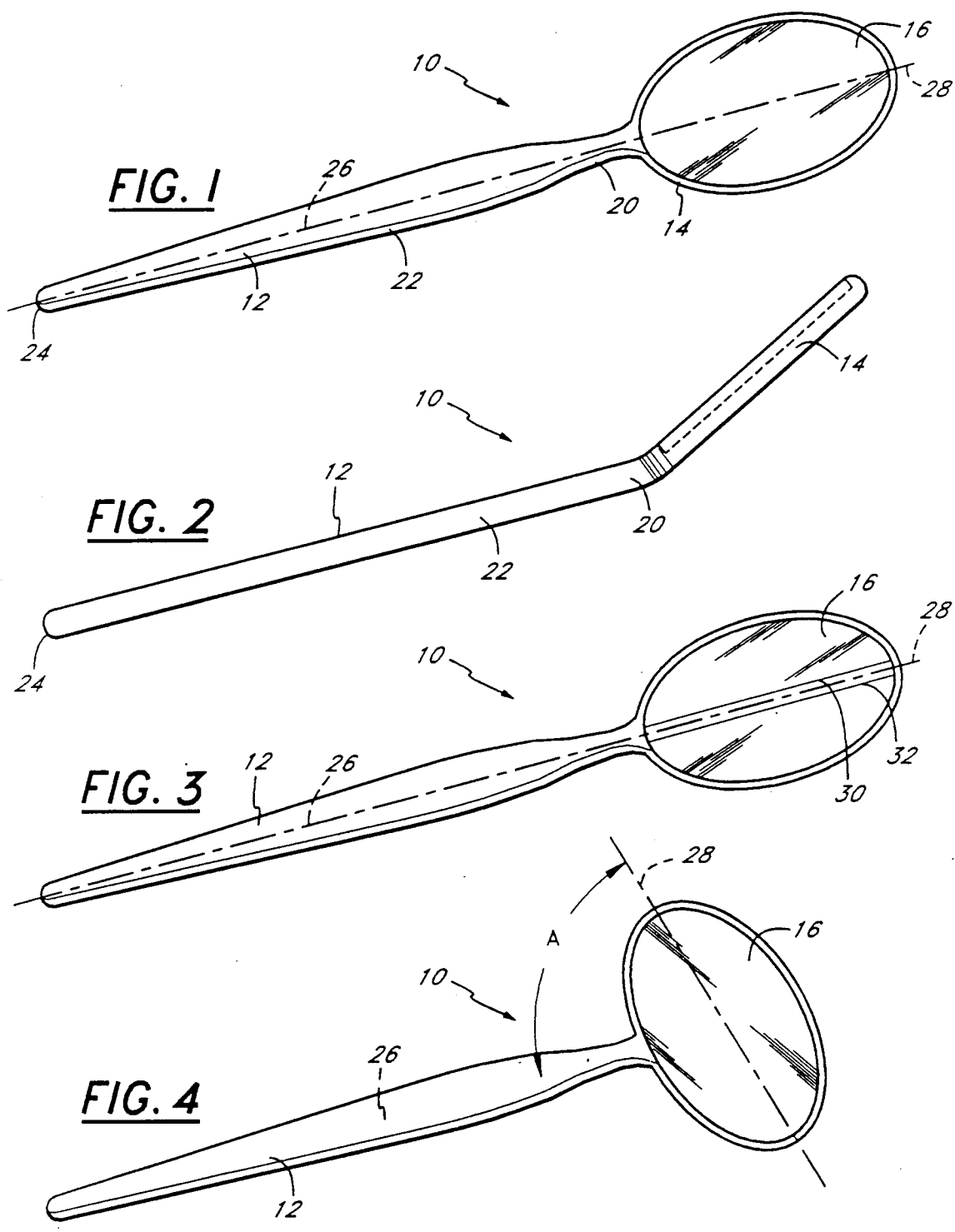

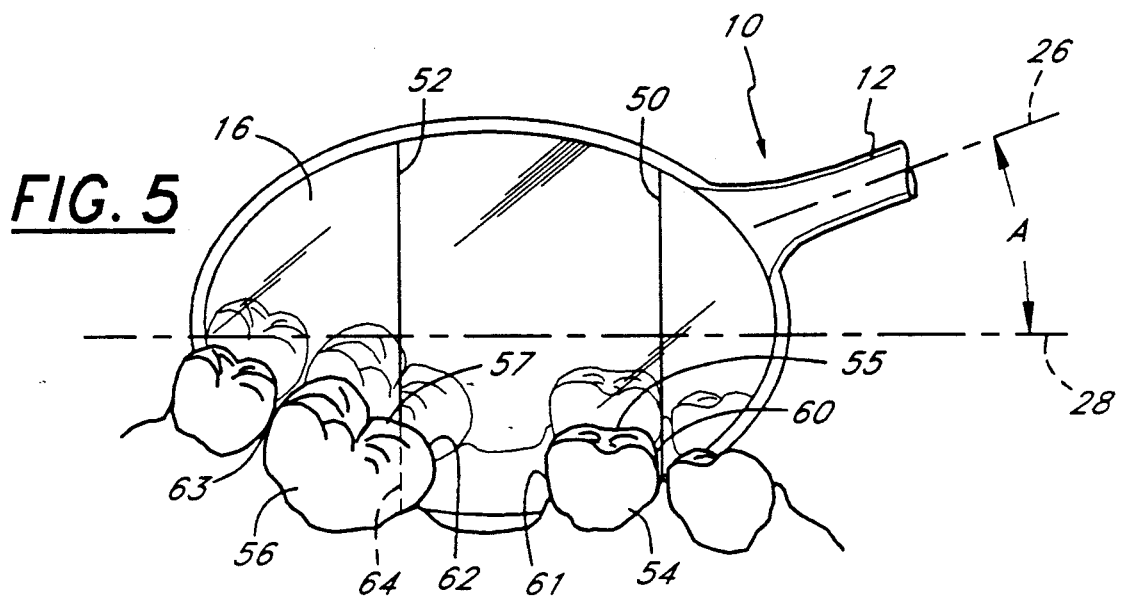
FIG. 5
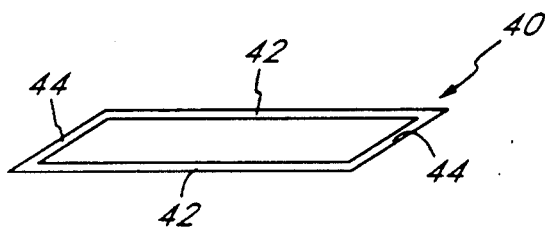
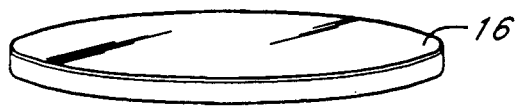
FIG. 6
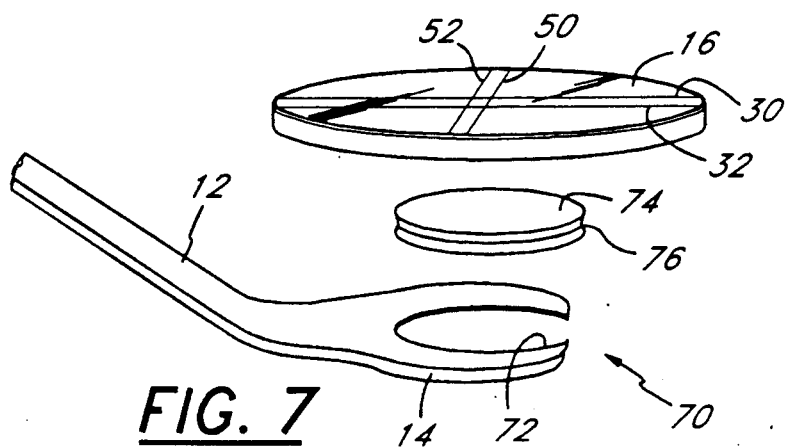
FIG. 7

DENTAL MIRROR AND METHOD OF USING SAME

BACKGROUND OF THE INVENTION

This invention relates to improvements in the field of dentistry. In particular, this invention relates to an improved dental mirror and method of using same.

In dentistry, there are relatively few choices when it comes to mouth mirrors. Essentially, such mirrors are limited to those having a round mirrored surface. This configuration has a number of advantages. It is easy and inexpensive to make. It also allows the mirror to be used in a wide range of dental applications. This configuration also has a number of drawbacks.

One drawback with conventional dental mouth mirrors is that the number of teeth which may be viewed using a conventional round mirror is extremely limited. For example, use of a conventional round mirror to view the abutment teeth during bridge preparation allows viewing of only 2 to 2 ½ teeth. This limited field of vision requires the operator to move the mirror axially with respect to the handle, in order to view the necessary surfaces of the teeth required for bridge preparation. Of course, the operator cannot see all the teeth involved in bridge preparation at once.

Another drawback with conventional round dental mouth mirrors is that there is no way that an operator can determine, through the use of such mirror alone, whether the process of reduction of teeth has reached the desired level. For example, in preparing the abutment teeth for a level. For example, in preparing the abutment teeth for a bridge, the anterior and posterior abutments of the abutment teeth must be reduced to parallelism in order for the bridge to fit. Using the conventional mouth mirror, the reduction process must be halted, the mouth mirror must be removed from the mouth of the patient and the parallelism must be determined by placing the bridge or a template into the patient's mouth and into the desired location. If the abutment surfaces are not parallel, more reduction is needed and the process must be repeated for successive iterations until parallelism is reached. This trial and error process is time consuming and can be extremely fatiguing for the operator and the patient.

Another example of the drawbacks of conventional dental mouth mirrors is in cosmetic dentistry, such as application of porcelain anterior veneer facings. In that particular process, the operator must reduce the labial surfaces of the anterior teeth in a uniform manner to accept a uniform application of laminants. Use of a conventional round mouth mirror does not enable the operator to see all six of the anterior teeth. In addition, the operator has no guide by which to reduce the labial surfaces in a uniform manner. Accordingly, the operator must reduce a particular tooth surface by guessing. Then the operator must move the mirror so as to view various portions of the anterior teeth for comparison. Only by performing a number of iterations of this process can the operator achieve uniform reduction.

Therefore, the conventional round mouth mirror of the prior art suffers from three identifiable disadvantages. First, its field of view is limited. Second, it has no reference means by which the operator can determine when and if tooth reduction has achieved the desired state. Third, it requires the operator to move the mirror handle axially to change the field of view.

SUMMARY OF THE INVENTION

The present invention is directed to an improved dental mirror and method for using same. The dental mirror of the present invention has an elongated handle, a head integral with the handle and a mirrored surface for reflecting an image of the patient's teeth. The mirrored surface is substantially wider in a first direction than in a second direction and has its major axis disposed from the longitudinal axis of the handle by an angle of approximately 75'. This angle allows changing the field of view by merely rotating the mirror handle about its longitudinal axis. The improvement eliminates the need for the tiresome and distracting axial movement of the mirror handle. The mirrored surface is oval in shape. This oval shape of the mirrored surface affords a larger field of view, which allows viewing of more teeth than the conventional round shape. Further, the increased surface area of the mirrored surface affords improved illumination of the patient's mouth. In addition, the oval shape allows for greater retraction of oral tissues, which decreases the occurrence of damage to soft tissue caused by contact with the sharp or high-speed rotating dental tool. The shape of the mirrored surface also allows insertion of the mirror into the mouth of the patient with little obstruction, an advantage not shared by a larger version of the conventional round dental mouth mirror. In addition, the improved dental mirror of the present invention includes a plurality of spaced parallel reference lines on the mirrored surface substantially perpendicular to the major axis of the mirrored surface. These reference lines are used for aligning with abutment teeth surfaces so as to determine parallelism of the abutment teeth surfaces for facilitate preparation of these surfaces for bridge installation. The reference lines on the mirrored surface may be etched onto the mirror itself, or may be provided by other means, such as a removable template.

In another embodiment of the invention, an improved dental mirror allows increasing the range of view of the mirror and the retraction of oral tissue and facilitating uniform reduction of maxillary anterior teeth. This embodiment of the invention has an elongated handle and a head integral with the handle, the head having a planar mirrored surface for reflecting an image of the distal portion of the maxillary anterior teeth. The mirrored surface is oval in shape so as to increase the view of the maxillary interior teeth and to increase retraction of oral tissue. The mirrored surface has thereon a plurality of closely spaced parallel reference lines which are substantially parallel to the major axis of the mirrored surface. The operator may use these reference lines for aligning a first reference line with the incisal edge of the anterior teeth and may use the second reference line to provide a visible guideline for uniform reduction of the anterior teeth. Use of these reference lines eliminates the guesswork involved in reduction of the anterior teeth, enables the operator to reduce the labial surfaces of the anterior teeth in uniform manner, increases the operator's ability to reduce enough tooth structure for uniform application of laminants. This embodiment is especially useful in cosmetic dentistry, particularly in porcelain anterior veneer facings.

In a further embodiment of the dental mirror of the present invention, a mirrored surface is mounted on a head integral with an elongated handle. The mirrored surface is oval-shaped and rotatable with respect to the handle. In a particularly preferred embodiment, the mirrored surface is rotatable through an arc of at least approximately 75°. This allows the major axis of the oval mirrored surface to be aligned with the longitudinal axis of the handle, or rotated to the position particularly advantageous for viewing the abutment teeth during bridge preparation.

The method of determining parallelism in first and second tooth surfaces of a patient includes the steps of inserting into the mouth of the patient a dental mirror having a plurality of parallel reference lines on the mirrored surface thereof, aligning the mirrored surface so that an image of the first and second tooth surfaces becomes visible to the operator, aligning the first reference line of the mirrored surface with the image of the first tooth surface, and visually comparing a second reference line on the mirrored surface with the image of the second tooth surface to determine whether the second reference line is collinear or parallel with the second tooth surface. This method may be used in a variety of applications. For example, this method may be used wherein the first and second tooth surfaces are on the abutment teeth used to support a bridge, in which case the method facilitates preparation of these abutment teeth for installation of a bridge. The method may also be used wherein the first tooth surface is the incisal edge of the maxillary interior teeth and the second reference line is spaced from the first reference line the distance by which the operator desires to reduce the maxillary anterior teeth. This latter application allows uniform reduction of the maxillary anterior teeth during cosmetic dentistry.

Further features and advantages of the present invention will become apparent from the detailed description of preferred embodiments which follow, when taken together with the appended figures and claims.

BRIEF DESCRIPTION OF THE DRAWINGS

FIG. 1 is a top view of the improved dental mirror of the present invention.

FIG. 2 is a side view of the mirror of FIG. 1.

FIG. 3 is a top view of an improved dental mirror of the present invention having spaced parallel reference lines thereon.

FIG. 4 is a top view of an improved dental mirror of the present invention in which the major axis of the oval mirrored surface is inclined with respect to the longitudinal axis of the handle by an angle of approximately 75°.

FIG. 5 is a fragmentary perspective view of an improved dental mirror of the present invention having spaced parallel reference lines thereon as applied to a patient's abutment teeth.

FIG. 6 is an exploded perspective view of an oval mirrored surface for a dental mirror of the present invention by which spaced parallel reference lines are provided by a template removably secured to the mirrored surface.

FIG. 7 is an exploded perspective view of an embodiment of the present invention in which the oval mirrored surface is rotatable with respect to the mirror handle.

DETAILED DESCRIPTION OF THE PREFERRED EMBODIMENT

Referring to FIGS. 1 and 2, an oval dental mouth mirror 10, in accordance with the present invention, is shown. The mirror 10 has an elongated handle 12 and an enlarged head 14 integrally joined with said handle. The head 14 supports a planar mirrored surface 16.

The handle 12 is shown having a first end 20 adjacent the head 14 and a second, free end 24 distal the head 14. Between the first and second ends 20, 24 is shown an enlarged portion 22. The configuration of the handle 12 shown in FIGS. 1 and 2 is adapted for comfortable gripping by the operator. The operator's fingers may comfortable grasp the portion between the first end 20 and the enlarged portion 22. The free end 24 may extend beyond include apertures for hanging the mirror 10 for storage. The handle 12 need not take the form shown in FIGS. 1 and 2. In the alternative, a straight cylindrical handle may be employed. In addition, the surface of the handle need not be smooth as shown. The handle surface may be knurled or otherwise treated to improve the gripping characteristics thereof. The handle may be imprinted with the name of the maker or other decorative designs. The construction of the handle 12 is subject to many variations all of which are fully within the knowledge of one of ordinary skill in the art, and need no further discussion here.

The head 14 of mirror 10 is for supporting the mirrored surface 16. The head 14 is, therefore, enlarged in the direction perpendicular to the longitudinal axis of the handle 12 so as to provide support for mirrored surface 16. The head 14 may be attached to the mirrored surface 16 by any of a number of suitable adhesives, including common glues, epoxies and the like. The primary concern in the attachment of the head 14 to the mirrored surface 16 is that the means not be water permeable or toxic. In FIGS. 1 and 2, the head 14 is shown as part of a one-piece construction with the handle 12. This construction is extremely advantageous for a disposable mirror. Such a disposable mirror 10 may be conveniently and inexpensively molded of plastic or other suitable lightweight material. In the alternative, the handle 12 and head 14 may be formed in separate pieces. For example, where a disposable mirror head 14 and mirrored surface 16, and a permanent handle 12 are desired, the handle 12 may be formed so that the first end 20 takes the form of a male threaded end for attachment to a female threaded socket in the head 14. Other means for attaching a handle 12 to a head 14 are well within the knowledge of one of ordinary skill in the art and need no further discussion here.

As shown in FIG. 1, the handle 12 has a longitudinal axis 26. In FIG. 1, the longitudinal axis 26 of the handle 12 s collinear with, and consequently parallel to, the major axis 28 of the oval-shaped mirrored surface 16. The oval shape of the mirrored surface 16 may take the form of a true ellipse, or any other shape in which one dimension is substantially larger than the dimension perpendicular thereto An additional consideration in selecting the shape of the mirrored surface 16 is that there be no sharp corners that could injure the tissue in the mouth of a patient. Accordingly, it has been found that an oval shape is particularly preferred. The primary advantage of the oval shape of the mirrored surface 16 is that the elongated length along the major axis 28 allows viewing a greater number of teeth than the conventional round dental mouth mirror. Further, the oval shape, with its increased area if the mirrored surface 16, affords increased illumination of the patient's mouth. The increased illumination allows easier and better observation of the teeth. In addition, the elongated length affords greater retraction of oral tissue away from the teeth being viewed and upon which dental work is being undertaken. This increase in retraction of oral tissue helps to prevent injury to that tissue by moving the tissue away from contact with sharp or high-speed rotating dental instruments. The oval shape allows the distance along the minor axis of the mirrored surface to remain substantially that of a conventional round dental mouth mirror. Accordingly, the oval shape allows easy insertion and retraction of the mirror 10 into and out of the mouth of a patient. Therefore, the oval shape allows an increase in the range of view of the mirror, an increase in illumination in the mouth, an increase in the retraction of oral tissues and avoids the obstruction that would accompany a larger size version of the conventional round dental mouth mirror.

Referring to FIGS. 1 and 2, the mirror 10 may be used to view distal portions of teeth within the mouth of a dental patient by inserting the mirrored surface 16 into the mouth of a patient, inserting &he mirrored surface 16 between the distal portion of the teeth and the tissue within the patient's mouth so as to retract the tissue away from the teeth, and viewing a reflection of the distal portion of the teeth in the mirrored surface 16.

Referring to FIG. 3, the oval dental mouth mirror of FIGS. 1 and 2 is shown with the addition of a plurality of spaced parallel reference lines 30, 32 on the mirrored surface 16. These lines may be etched, scribed or otherwise provided on the mirrored surface. As shown in FIG. 6, there reference lines 30, 32 may also be provided on the mirrored surface 16 by means of a template 40 releasably attached to the mirrored surface 16. The template 40 has a pair of thin, spaced parallel bars 42 that act as reference lines 30, 32 when attached to the mirrored surface 16. The bars may be are joined at the ends thereof by a pair of connecting bars 44 as shown. These connecting bars 44 act to space the bars 42 and keep them parallel. The template 40 may be formed of a "peel-and-stick" material such as water-impermeable paper or plastic backed with an adhesive. Alternatively, the template 40 could be formed of relatively rigid molded plastic and be supplied with hooks or other means for removably securing the template 40 to the mirrored surface 16. Such a disposable template 40 would be advantageous for use with a permanent mirror 10 or could be provided in different spacings to add versatility to a mirror 10 without reference lines. For example, templates 40 could be provided with different spacings between the reference lines thereof and with orientations parallel or perpendicular to the major axis of the oval mirrored surface 16. Similarly, such a template 40 could be used on conventional round dental mouth mirrors, as could scribed or etched reference lines. One of ordinary skill in the art will recognize alternative means for providing spaced parallel reference lines on the face of a mirrored surface. In addition, one of ordinary skill in the art will recognize that the template disclosed above may be modified in a number of ways.

Returning to FIG. 3, the oval dental mirror 10 has closely-spaced, parallel lines 30, 32 parallel to the major axis 28 of the mirrored surface 16, which major axis 28 is parallel to the major axis 26 of the mirror handle 12. This embodiment is useful in cosmetic dentistry. In particular, the mirror 10 is useful in the cosmetic dentistry process of porcelain anterior veneer facings. In order to reduce the labial surfaces of the anterior teeth in a uniform manner so as to accept a uniform layer of laminants, the operator inserts the mirror 10 into the mouth of the patient, aligns the mirrored surface 16 so that the distal portion of the maxillary anterior teeth is reflected therein, and so that an image of the distal portion of the maxillary anterior teeth becomes visible. The operator then aligns a first reference line 30 with the incisal edge by the axillary anterior teeth. The second reference line 32 is spaced below the first reference line 30 the distance by which the maxillary anterior teeth are desired to be reduced. This second reference line 32 provides a reference line on the mirrored surface 16. The operator visually compares the second reference line 32 with the image of the incisal edge of the maxillary anterior teeth as the operator reduces those teeth to determine when the second reference line is collinear or parallel with the new incisal edge.

Referring to FIG. 4, another preferred embodiment of the dental mouth mirror 10 of the present invention is shown. In the embodiment of FIG. 4, the major axis 28 of the mirrored surface 16 is disposed from the longitudinal axis 26 of the handle 12 by an angle A. It has been found by studying many models and examples of human dentition that this angle A is preferably approximately 75°. Incorporating this angle A into a dental mouth mirror allows alignment of the mirrored surface 16 in the patient's mouth so that the handle is conveniently arranged with respect to the patient's mouth and the operator's hand. This angle A allows the operator to change the field of view by merely changing the angle of the mirror handle longitudinal axis 26, a simple rotational movement of the wrist. This improvement eliminates the need for the tiresome and distracting axial movement of the mirror handle 12. The angle A is preferably approximately 75°. Of course, one of ordinary skill in the art will recognize that the angle may be reversed to accommodate a left-handed operator. That is, the angle A may be provided as approximately 105° for left-handed operators. Of course the complementary angle would be approximately 75°.

Referring to FIG. 5, the oval dental mouth mirror 10 of the present invention is shown in a fragmentary view as used in preparing teeth for bridge installation. The oval mirror 10 is shown with the angle A between the major axis 28 of the mirrored surface 16 and the longitudinal axis 26 of the handle 12, preferably approximately 75°. The mirrored surface 16 has provided thereon first and second spaced, parallel, vertical reference lines 50 and 52. These reference lines 50, 52 may be used to determine parallelism is the abutment teeth 54, 56, those used to attach bridgework. To prepare the abutment teeth 54, 56, the mirror 11 is inserted into the patient's mouth and placed on the buccal or lingual vestibule facing either the buccal or lingual aspect of the abutment teeth 54, 56. The mirror 10 need not be rested on the buccal or lingual vestibule, but such resting enhances the stability of the mirror 10 any consequent stability of the image therein. The mirrored surface 16 is aligned so that the distal surfaces 55, P7 of the abutment teeth 54, 56 are reflected therein and so that an image of the distal surfaces 55, 57 becomes visible to the operator. The operator then aligns the first reference line 50 with the image of an edge 60 of the first abutment tooth distal surface 55. The operator then visually compares the second reference line 52 with the second abutment tooth distal surface 57 to determine whether the edge 62 thereof is parallel to or collinear with the second reference line 52, and also the first reference line 50 and first abutment tooth surface edge 60. If it is not, the operator must reduce the second tooth 56, preferably while viewing the tooth 56 in the mirror 10 and comparing the edge 62 with the second reference line 52, until the edge 62 is parallel with the image of the edge 60. For example, in FIG. 5, the operator would reduce the tooth 56 to remove the tooth area bounded by the broken line 64. Once the edges 60 and 62 are parallel, the operator may continue on to determine parallelism between the remaining edges 61, 63, as well as parallelism between the now-parallel edges 60, 62 and those remaining edges 61, 63. Once the four edges 60–63 are parallel, the abutment teeth 54, 56 are ready installation of a bridge. The operator then repeats the process for the abutment teeth on the other side of the patient's mouth. The foregoing method is particularly useful in preparing mesially-inclined abutment teeth. In such a situation, the mesially-inclined posterior or anterior abutment teeth are difficult to render parallel using the old method of guessing when sufficient reduction has been achieved.

Referring to FIG. 7, an adjustable dental mouth mirror 70 is shown in exploded perspective view. The handle 12 of the mirror 70 is integrally attached to the head 14. The head 14 has disposed therein a slot 72. This slot 72 is adapted to rotatably receive therein mounting disk 74. The mounting disk 74 has a groove 76 disposed along its outer periphery. The groove 76 is configured to conform with the inner surface of this slot 72 so as to allow rotation of the mounting disk 74 with respect to the head 14. The mounting disk 74 is configured to attach to the mirrored surface 16 by means of a suitable adhesive or the like. By fixing the mirrored surface 16 with respect to the mounting disk 74, the mirrored surface 16 is made rotatable with respect to the mirror head 14 and the handle 12 The mirrored surface 16 is shown formed in the oval shape of the preferred embodiment of the present invention. The mirrored surface 16 may contain thereon first and second reference lines 30, 32 parallel to the major axis 28 of the oval mirrored surface 16. Likewise, the mirrored surface 16 may contain first and second reference lines 50, 52 perpendicular to the major axis 28 of the oval mirrored surface 16. Alternatively, reference lines may be employed with the embodiment of FIG. 7 by means of a template, as shown in FIG. 6. The adjustable oval mirror 70 of FIG. 7 is preferably designed so that the mirrored surface 16 is rotatable with respect to the handle 12 through an arc of at least approximately 75° from a position in which the major axis of the mirrored surface 16 is parallel with the longitudinal axis of the handle 12. This allows the mirror to be used for various applications, as discussed above. The adjustable mirror 70 of FIG. 7 may be used in various embodiments, including use of a conventional round mirrored surface 16 having reference lines thereon The means by which the mirrored surface 16 may be made rotatable with respect to the handle 12 is relatively unimportant to the concept of the invention. One of ordinary skill in the art would be able to devise a number of alternate means for providing the rotatable relationship between the mirrored surface 16 and the handle 12 of the adjustable mirror 70.

The improved dental mirror and method of using same has been disclosed in detail in connection with the preferred embodiments, but these embodiments are disclosed by way of examples only and are not to limit the scope of the present invention, which is defined by the claims that follow. One of ordinary skill in &:he art will appreciate many variations and modifications within the scope of this invention.

What is claimed is:

1. An improved dental mirror for increasing the range of view of the mirror, illumination of the mouth and the retraction of oral tissue, for facilitating changing views by merely changing the angle of the handle, and for facilitating preparation of abutment teeth for bridge installation, comprising:
    an elongated handle having a first end and a longitudinal axis;
    a head integral with said handle at said first end, said head having a substantially planar mirrored surface for reflecting an image of the patient's teeth, said mirrored surface being oval-shaped with its major axis being disposed from said longitudinal axis of said handle by an angle of approximately seventy five degrees; and
    a plurality of spaced parallel reference lines on said mirrored surface substantially perpendicular to said major axis of said mirrored surface for aligning with abutment teeth surfaces so as to determine parallelism of said abutment teeth surfaces.

2. The mirror of claim 1, wherein said oval-shape is an ellipse.

3. The mirror of claim 1, wherein said reference lines are etched on said mirrored surface.

4. The mirror of claim 1, wherein said reference lines are provided by a disposable template removably secured to said head.

5. The mirror of claim 1, wherein said handle is removable from said head.

6. An improved dental mirror for increasing the range of view of the mirror, illumination of the mouth and the retraction of oral tissue and facilitating uniform reduction the labial surfaces of maxillary anterior teeth, comprising:
    an elongated handle for gripping having a first end;
    a head integral with said handle at said first end having a planar mirrored surface whereby an image of the distal portion of the maxillary anterior teeth may be reflected said mirrored surface being oval-shaped whereby the view of said maxillary anterior teeth and retraction of oral tissue are increased; and
    a plurality of closely-spaced parallel reference lines on said mirrored surface substantially parallel to the major axis of said mirrored surface for aligning a first of said reference lines with the incisal edge of said anterior teeth and using a second of said reference lines to provide a visible guide line for uniform reduction of said labial surfaces of said anterior teeth.

7. An improved method of determining parallelism in first and second tooth surfaces of a patient, comprising the steps of:
    inserting into the mouth of a patient a dental mirror having a plurality of spaced parallel reference lines on the mirrored surface thereof;
    aligning said mirrored surface so that said first and second tooth surfaces are reflected therein and so that an image of said first and second tooth surfaces becomes visible;
    aligning a first reference line on said mirrored surface with said image of said first tooth surface; and
    visually comparing a second reference line on said mirrored surface with said second tooth surface to determine whether said second reference line is parallel with said second tooth surface.

8. The method of claim 7, wherein said first and second tooth surfaces are on the abutment teeth used to support a bridge, whereby said method facilitates preparation of said abutment teeth for installation of a bridge.

9. The method of claim 7, wherein said first tooth surface is the incisal edge of the maxillary anterior teeth and said second reference line is spaced from the first reference line the distance by which said maxillary anterior teeth are desired to be reduced, whereby said method allows uniform reduction of the maxillary anterior teeth.

10. An improved method of viewing abutment teeth of a dental patient during bridge preparation, comprising the steps of:
providing a dental mirror having an elongated handle with a first end and a longitudinal axis, a head integral with said handle at said first end having a planar, oval-shaped mirrored surface with its major axis disposed from said longitudinal axis of said handle by an angle of approximately 75°;
inserting said mirrored surface into the mouth of a dental patient;
inserting said mirrored surface between the distal portion if said patient's abutment teeth and tissue within said patient's mouth so as to retract said tissue from said teeth; and
aligning said mirrored surface so that an image of said distal portion of both of said patient's abutment teeth becomes visible, whereby preparation of said abutment teeth for installation of a bridge is facilitated.

* * * * *